Dec. 28, 1937. R. ZEPARO Plant Pat. 265
BEGONIA
Original Filed Oct. 31, 1935
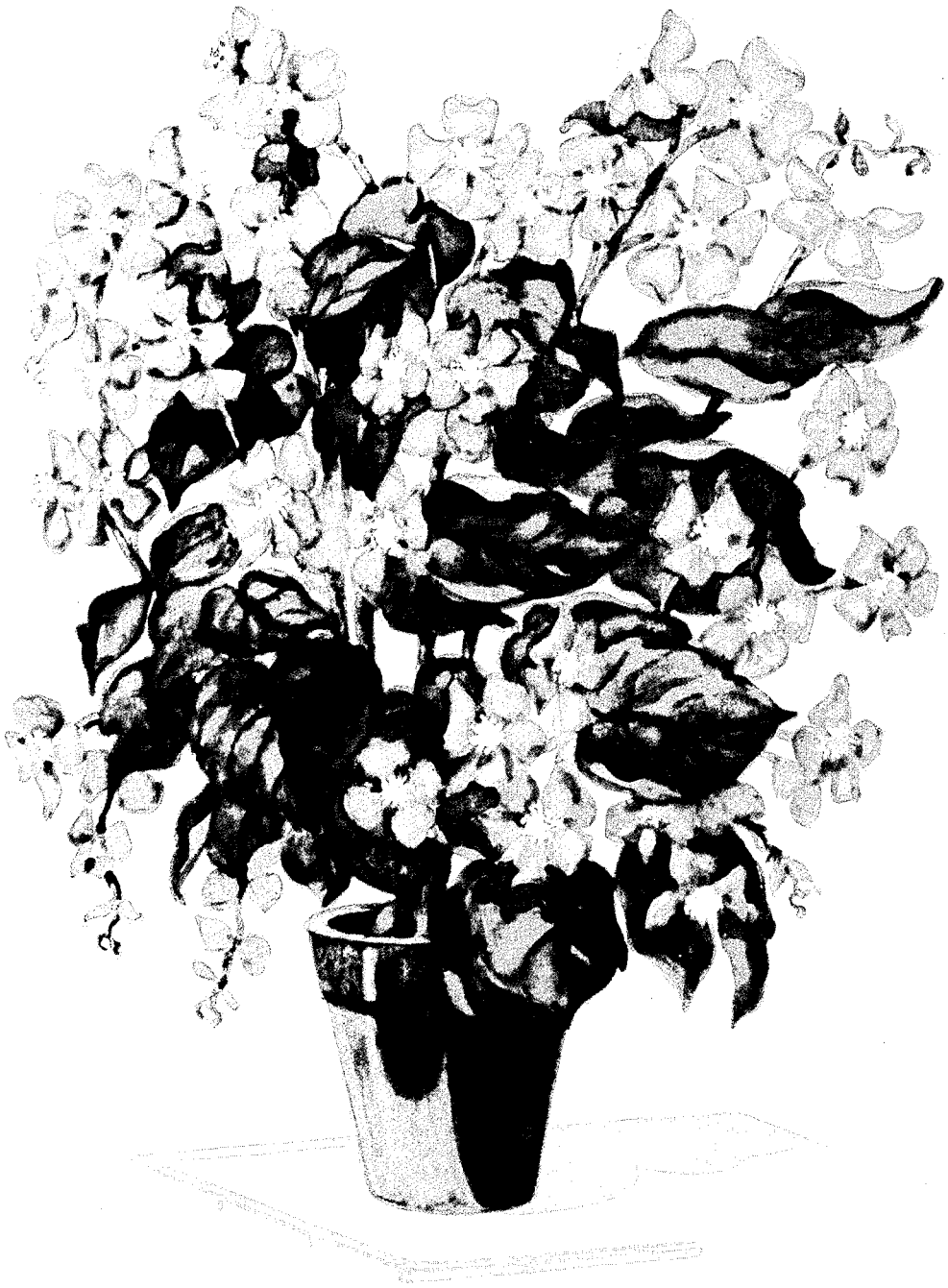
Inventor
Rocco Zeparo
By Fletcher Sprague Hyde
ATTORNEY.

Patented Dec. 28, 1937

Plant Pat. 265

UNITED STATES PATENT OFFICE

265

BEGONIA

Rocco Zeparo, Arlington, Mass.

Application October 31, 1935, Serial No. 47,707
Renewed July 23, 1937

1 Claim. (Cl. 47—59)

This discovery relates to a new variety of hybrid begonia which I first developed from a bud sport of the ordinary Winter Romance, which I crossed with *Begonia semperflorens streigau*, both well known varieties. The sport from the Winter Romance was the pollen parent and the *Begonia semperflorens streigau* the seed parent. The resulting begonia was asexually reproduced by me.

The new variety of begonia discovered and propagated by me is a large sized begonia plant with a flower of a peculiar and distinct salmon color, similar in appearance in many respects to both the above varieties, but having marked characteristics not possessed by either.

The new variety, however has several individual variations from the parent varieties. Its color is of a deeper and more salmon colored shade of red than the Winter Romance, the size of its petals is greater than those of the other varieties, and, when grown in hothouses, opens more freely and uniformly, retains its color more permanently and blooms with more continuity through a much longer season than any other known variety of begonia.

The Winter Romance begonia is highly regarded by florists, by reason of the color of its blooms, the fact that it can be successfully grown under glass, and that it can be "pinched back", that is, it can be trimmed by pinching off the ends of the branches, and it will under proper growing conditions, produce blooms again in four months. It is, however, weak growing, the blooms are seldom, if ever, more than 1¼ inches in diameter, and the maximum blooming season under favorable conditions, when the plant is grown by a skillful grower, in a hot-house, is not over two months at each blooming. It has, moreover, when watered by a spray or syringe, so that the foliage becomes moistened, a tendency to "damp off". By "damping off" is meant the tendency of certain hot-house plants to rot after watering the foliage, or when any unusual humidity occurs in the hot-houses. The "damping off" causes the plant on which it has any effect to be without value when it occurs, and the plants affected by it have to be destroyed. The *Begonia semperflorens streigau* is also well known to florists for its dark-colored, almost red, flowers, which have peculiar color and beauty, but this variety, when grown in hot-houses is particularly subject to disease. Almost all the plants of this variety grown under glass become infected. If plants of this variety are "pinched back", the plant does not successfully break out in foliage or bloom. The plants are slow to grow and have a weak bloom which lasts from three days to two weeks. This plant is particularly subject to "damping off".

The new variety of begonia discovered and propagated by me is much superior to either of the above varieties or to an ordinary crossing of these two plants as contrasted to the plant propagated by me from the crossing of the bud sport of the Winter Romance with the *semperflorens streigau*. The new variety has blooms over the entire plant which appear with uniformity, and are on the average 2½ inches in diameter when the blooms are fully expanded. The blooming season of the new variety is, on the average, six months. The plant can be "pinched back" and will grow again in two months, as contrasted with the Winter Romance which takes four months to grow again, and the *Begonia semperflorens streigau*, which after "pinching back" does not grow well at all. The Winter Romance has a furry surface on the leaf, while the begonia discovered and propagated by me has smooth leaves.

One of the main advantages of the new variety is that it is a practical begonia for commercial growing in hot-houses since it does not have a tendency to "damp off" and the plants are remarkably resistant to disease.

Since the discovery of the sport, I have succeeded in propagating the new variety in quantity and in making permanent the advantageous charactertistics of the original plant, and have, at the present time, a large number of plants of the new variety which are producing blooms of the color herein illustrated and described.

The accompanying illustrations show in full color the characteristic foliage and blooms, both partially opened and fully opened flowers.

The petals of the new variety of begonia are similar in shape to those of the Winter Romance, but the color is much deeper than the petals of this variety, and not red like the petals of the *Begonia semperflorens streigau*.

The leaves of my new variety of begonia are dark green, glossy, and very slightly cupped. The stems are green, with some admixture of red when the plant is young, becoming more red toward the base as the plants mature. The plants bloom freely and continuously. There is very little difference in the color of the petals upon the inner and the outer surfaces. The outer edges of the petals are slightly darker than the inner. In a rather cold north light, without sunshine, the color of the petals is fairly well matched by Plate XXVI of Ridgeway, Color Standards, published by the author, Robert Ridgeway, Washington, D. C.

1912, and shades from the outer edge of the petals from the color indicated as Spinel red, through Spinel pink, to the color indicated as Thulite pink.

Another advantageous characteristic of the new variety is that the petals retain their deep color after the blooms have been fully opened for some time. When the flowers are brought nearer the sunlight, the pitch of all the colors rises to a greater degree of brilliance.

I have produced, therefore, a new variety of begonia which produces flowers of large size and of great beauty, which retain their brilliance after opening, and have no tendency to be affected by rot after the plant is watered or exposed to an extraordinary degree of humidity.

This begonia is particularly adapted for growing by the florist and decorative plant trade.

The plant is compact; when fully grown it is 18 to 24 inches in height with thick heavy stem 3½ inches in circumference at the base on the average; it is 50% more rapid in attaining full growth and coming into bloom, than its parents. Leaves are unusually large and uniform. Blooms have large yellow center 1 inch to 1½ inches in diameter. Seeds do not germinate.

I claim:

The begonia plant of parentage *semperflorens streigau* × sport of Winter Romance, substantially as herein shown and described, characterized in that it bears an unusually large flower of deep salmon color, blooms for six months, is resistant to plant disease and not subject to damping-off, and puts out, when cultivated in hothouses, new foliage and flowers in two months after cutting back.

ROCCO ZEPARO.